US010595963B2

(12) United States Patent
Miyano et al.

(10) Patent No.: US 10,595,963 B2
(45) Date of Patent: Mar. 24, 2020

(54) DISPENSER, AND DISPENSER AND CARTRIDGE

(71) Applicant: GC Corporation, Shizuoka (JP)

(72) Inventors: Tatsunosuke Miyano, Tokyo (JP); Shigeaki Matsunaga, Tochigi (JP)

(73) Assignee: GC Corporation, Shizuoka (JP)

( * ) Notice: Subject to any disclaimer, the term of this patent is extended or adjusted under 35 U.S.C. 154(b) by 0 days.

(21) Appl. No.: 16/098,256

(22) PCT Filed: Apr. 26, 2017

(86) PCT No.: PCT/JP2017/016625
§ 371 (c)(1),
(2) Date: Nov. 1, 2018

(87) PCT Pub. No.: WO2017/208692
PCT Pub. Date: Dec. 7, 2017

(65) Prior Publication Data
US 2019/0142549 A1 May 16, 2019

(30) Foreign Application Priority Data
Jun. 1, 2016 (JP) .................................. 2016-109927

(51) Int. Cl.
*A61C 5/64* (2017.01)
*B05C 17/01* (2006.01)
(52) U.S. Cl.
CPC ................ *A61C 5/64* (2017.02); *B05C 17/01* (2013.01)
(58) Field of Classification Search
CPC .................................... A61C 5/64; B05C 17/01
(Continued)

(56) References Cited

U.S. PATENT DOCUMENTS 4,382,789 A * 5/1983 Colombo .............. A61M 5/315
433/89
4,526,303 A * 7/1985 Harrod ............... A61B 17/8822
222/386

(Continued)

FOREIGN PATENT DOCUMENTS

GB 2172059 9/1986
JP S62-290453 12/1987
(Continued)

OTHER PUBLICATIONS

International Search Report for PCT/JP2017/016625 dated Aug. 1, 2017.

*Primary Examiner* — Patrick M. Buechner
*Assistant Examiner* — Michael J. Melaragno
(74) *Attorney, Agent, or Firm* — IPUSA, PLLC

(57) ABSTRACT

A dispenser includes a guide shaft, a housing, accommodating the guide shaft, and supporting the guide shaft movably frontward and rearward along an axial direction, a slide block slidably mounted on the guide shaft, a piston shaft having one end mounted on the slide block, and another end projecting from the housing as the slide block moves frontward, a handle projecting from the housing, a slide bar having one end rotatably supported on the housing, and another end approaching the handle when rotated, and an engaging piece provided on the one end of the slide bar and engaging a guide groove formed in the guide shaft, wherein the engaging piece moves the guide shaft frontward when the other end of the slide bar is rotated to approach the handle due to an operation of a user.

10 Claims, 6 Drawing Sheets

(58) Field of Classification Search
USPC .......................................... 222/323; 433/89
See application file for complete search history.

(56) References Cited

U.S. PATENT DOCUMENTS

| | | | |
|---|---|---|---|
| 4,693,684 A | 9/1987 | Blatherwick et al. | |
| 4,994,065 A * | 2/1991 | Gibbs | A61B 17/8822 222/391 |
| 5,192,008 A * | 3/1993 | Hwan | B05C 17/01 222/326 |
| 5,464,131 A * | 11/1995 | Keller | B05C 17/00553 222/391 |
| 5,823,403 A * | 10/1998 | Schneider | B05C 17/01 222/391 |
| 5,871,354 A | 2/1999 | Kunkel et al. | |
| 6,296,484 B1 * | 10/2001 | Nihei | B05C 17/00553 222/391 |
| 6,766,923 B1 * | 7/2004 | Huang | B05C 17/01 222/327 |
| 7,306,125 B2 * | 12/2007 | Takahashi | B05C 17/0123 222/153.13 |
| 7,344,375 B2 * | 3/2008 | Mukasa | A61C 5/62 222/391 |
| 2003/0192916 A1 * | 10/2003 | Watson | B05C 17/01 222/391 |
| 2006/0175356 A1 | 8/2006 | Takahashi et al. | |
| 2012/0031931 A1 | 2/2012 | Strobel-Schmidt et al. | |

FOREIGN PATENT DOCUMENTS

| | | |
|---|---|---|
| JP | H10-43206 | 2/1998 |
| JP | 2003-212278 | 7/2003 |
| JP | 2005-328978 | 12/2005 |
| JP | 3761626 | 3/2006 |
| JP | 2006-217962 | 8/2006 |
| JP | 2012-011381 | 1/2012 |

* cited by examiner

DISPENSER, AND DISPENSER AND CARTRIDGE

TECHNICAL FIELD

The present invention relates to a dispenser, and a dispenser and cartridge.

BACKGROUND ART

For example, a known dispenser dispenses a dental viscous material filled in a cartridge, a predetermined amount at a time, when a lever is operated to squeeze the lever together with a case member, to move a piston rod provided within the case member (for example, refer to Patent Document 1).

PRIOR ART DOCUMENTS

Patent Documents

Patent Document 1: Japanese Laid-Open Patent Publication No. 10-43206
Patent Document 2: Japanese Laid-Open Patent Publication No. 2003-212278

DISCLOSURE OF THE INVENTION

Problem to be Solved by the Invention

According to the dispenser of Patent Document 1, it is difficult to finely adjust a direction, a position, or the like of the material that is ejected from the cartridge, because the lever is operated to squeeze the lever together with the case member, and there is room for improvement of the operability.

The present invention is conceived in view of the above circumstances, and one object is to provide a dispenser having an improved operability.

Means of Solving the Problem

According to one embodiment of the present invention, a dispenser includes a guide shaft, a housing, accommodating the guide shaft, and supporting the guide shaft movably frontward and rearward along an axial direction, a slide block slidably mounted on the guide shaft, a piston shaft having one end mounted on the slide block, and another end projecting from the housing as the slide block moves frontward, a handle projecting from the housing, a slide bar having one end rotatably supported on the housing, and another end approaching the handle when rotated, and an engaging piece provided on the one end of the slide bar and engaging a guide groove formed in the guide shaft, wherein the engaging piece moves the guide shaft frontward when the other end of the slide bar is rotated to approach the handle due to an operation of a user.

Effects of the Invention

According to embodiments of the present invention, it is possible to provide a dispenser having an improved operability.

MODE OF CARRYING OUT THE INVENTION

Figure 1:
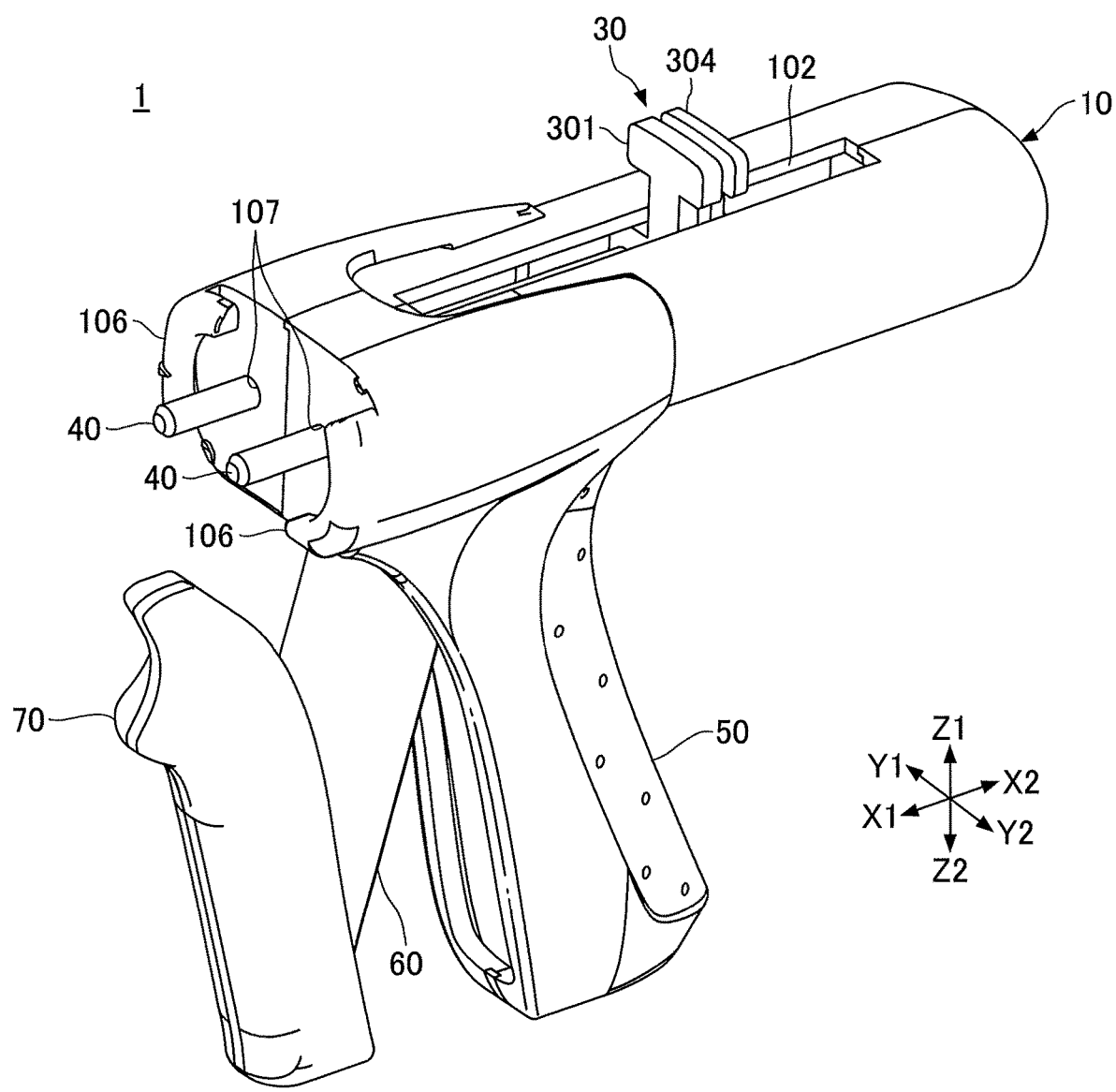
FIG. 1 is a perspective view illustrating an example of a dispenser in one embodiment.

Embodiments of the present invention will be described, by referring to the drawings. In each of the drawings, those constituent parts that are the same are designated by the same reference numerals, and a repeated description of the same parts may be omitted.

Figure 2:
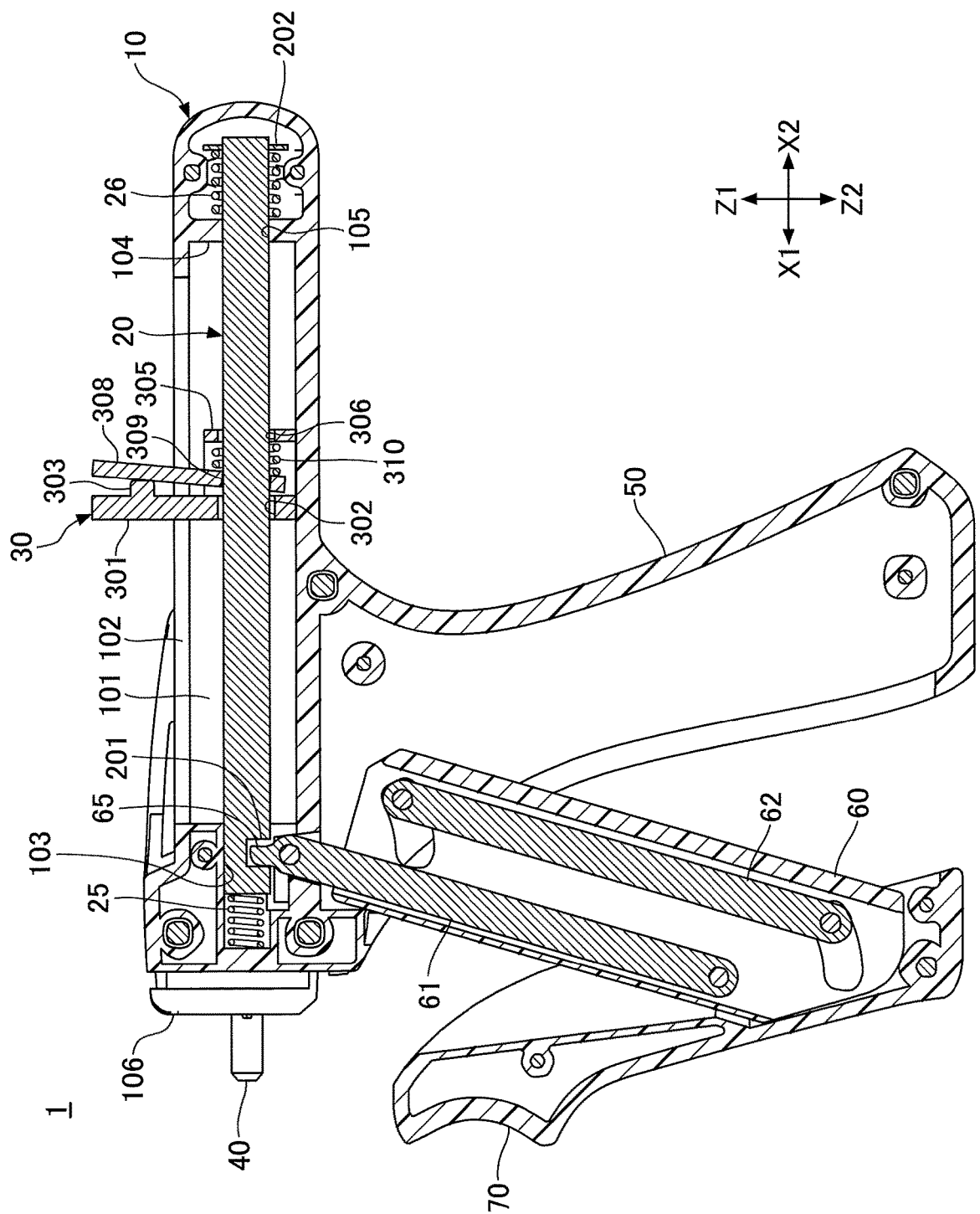
FIG. 2 is a view in a longitudinal cross section (part 1) illustrating the example of the dispenser in one embodiment.
Figure 3:
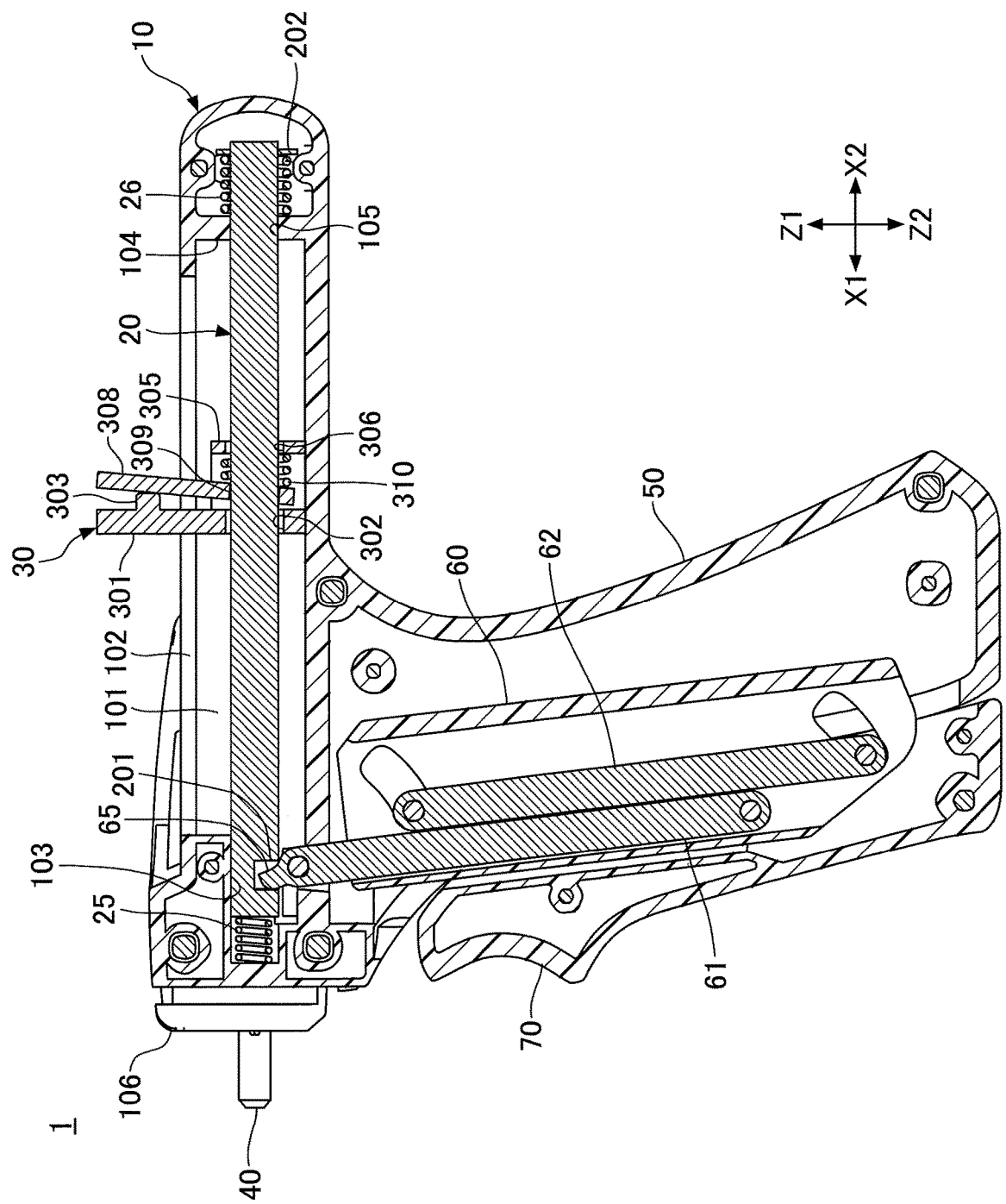
FIG. 3 is a view in a longitudinal cross section (part 2) illustrating the example of the dispenser in one embodiment.
Figure 4:
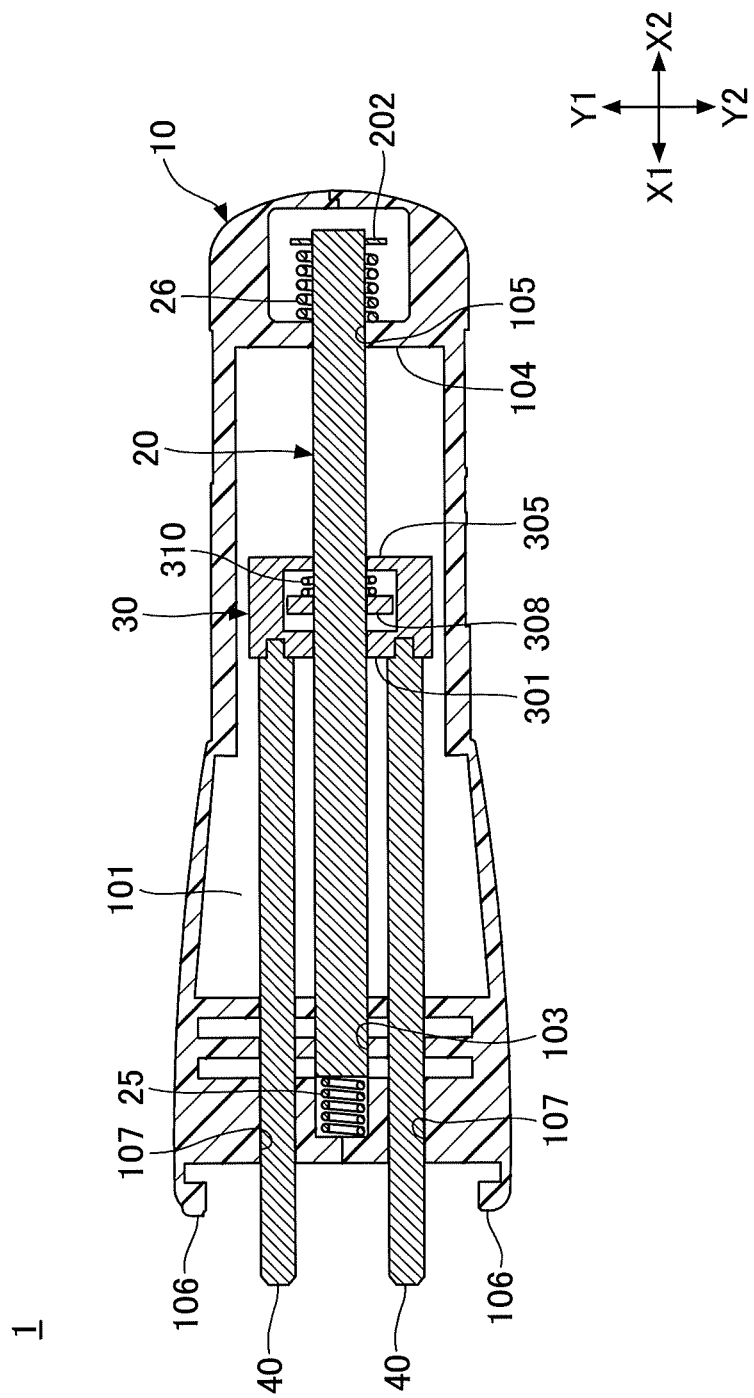
FIG. 4 is a view in a transverse cross section illustrating the example of the dispenser in one embodiment.
Figure 5:
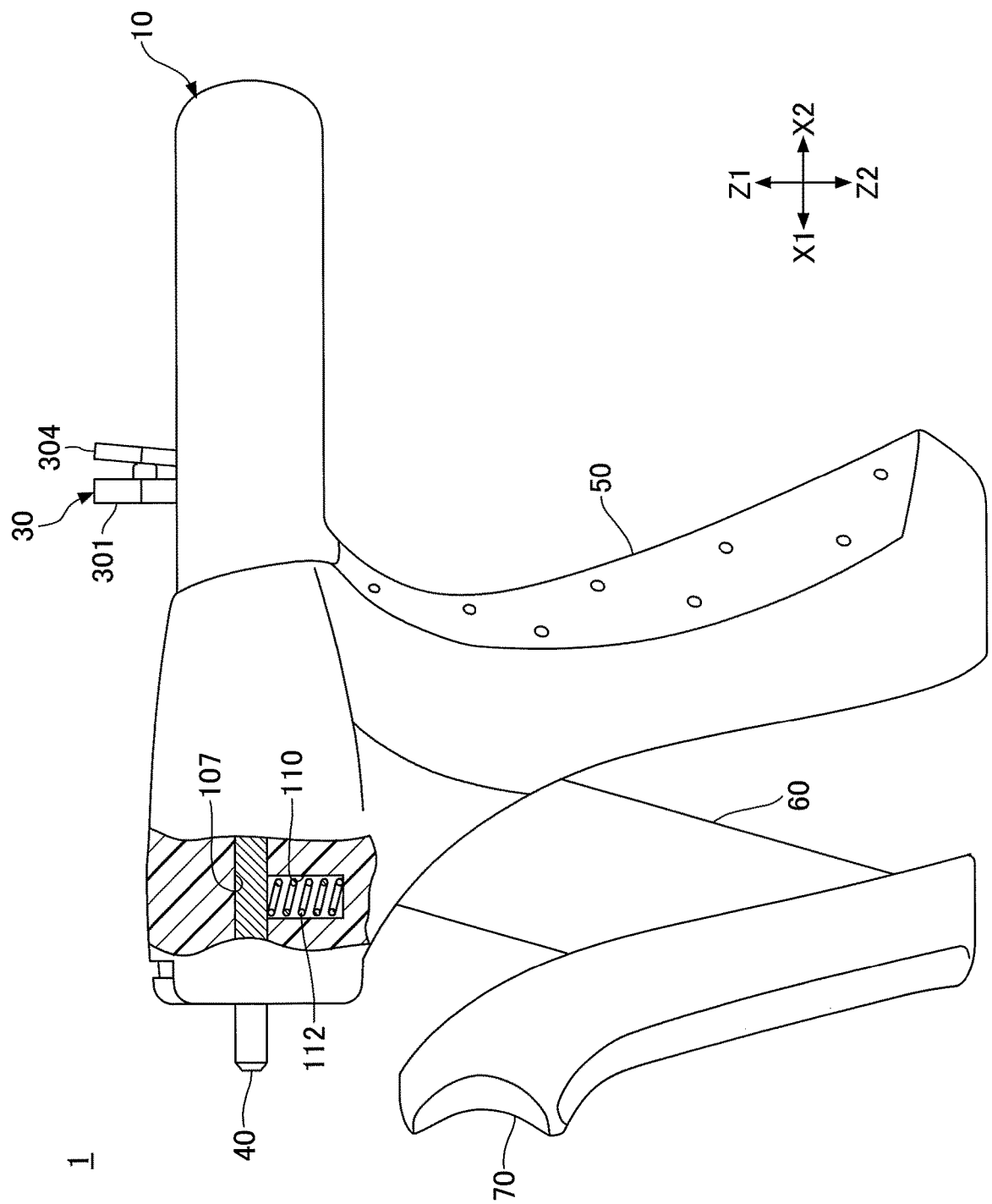
FIG. 5 is a view in a partial cross section illustrating the example of the dispenser in one embodiment.

FIG. 1 is a perspective view illustrating an example of a dispenser 1 in one embodiment. FIG. 2 and FIG. 3 respectively are views in a longitudinal cross section illustrating the example of the dispenser 1 in one embodiment. FIG. 2 illustrates the example of the dispenser 1 before a user squeezes a lever 70. In addition, FIG. 3 illustrates the example of the dispenser 1 after the user squeezes the lever 70. FIG. 4 is a view in a transverse cross section illustrating the example of the dispenser 1 in one embodiment. FIG. 5 is a view in a partial cross section illustrating the example of the dispenser 1 in one embodiment.

As illustrated in each of the drawings, X1 and X2 directions indicate a front direction and a rear direction of the dispenser 1, respectively. In addition, Y1 and Y2 directions indicate a right direction and a left direction of the dispenser 1, respectively, and Z1 and Z2 directions indicate an up direction and a down direction of the dispenser 1, respectively. In the following description, the X1 direction may also be referred to as frontward, the X2 direction may also be referred to as rearward, the Z1 direction may also be referred to as upward, and the Z2 direction may also be referred to as downward.

As illustrated in FIG. 1 through FIG. 5, the dispenser 1 includes a housing 10, a guide shaft 20, a slide block 30, piston shafts 40, a handle 50, a bar cover 60, a first slide bar 61, a second slide bar 62, and a lever 70.

The housing 10 is made of a resin material such as an engineering plastic or the like, or a light and strong material such as a light metal that may be an aluminum alloy or the like, for example, and is formed to a rectangular box shape. The housing 10 includes an accommodating space 101 that accommodates the guide shaft 20 and the slide block 30, and an opening 102 formed above the accommodating space 101.

As illustrated in FIG. 2 through FIG. 4, a front support hole 103 for supporting a front end part of the guide shaft 20 is formed in front of the accommodating space 101 of the housing 10. In addition, a rear support hole 105 for supporting a rear end part of the guide shaft 20 is formed in a rear end support wall 104 at the rear of the accommodating space 101.

Figure 6:
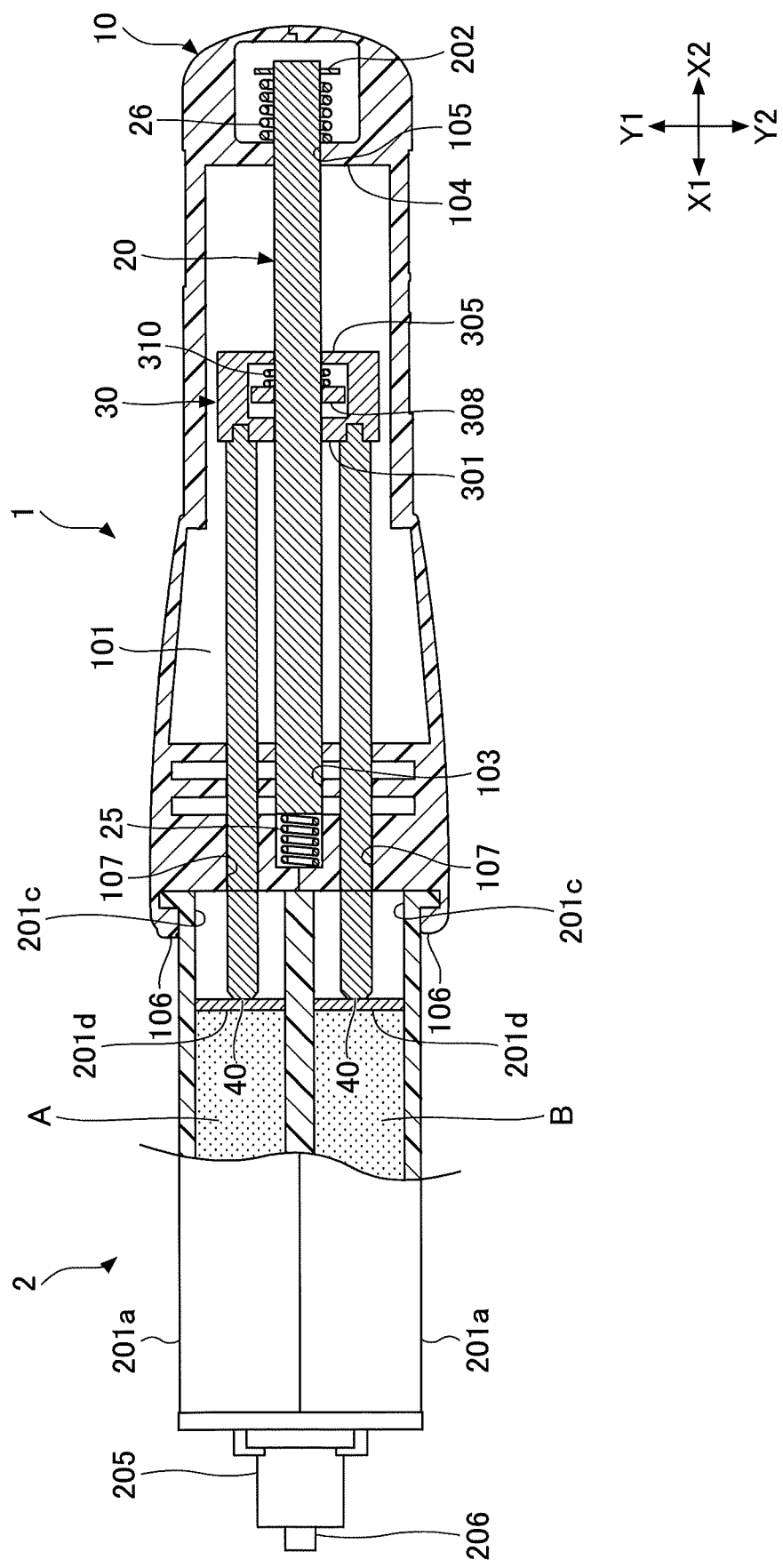
FIG. 6 is a view in a partial cross section illustrating an example of a state in which a cartridge is mounted on the dispenser in one embodiment.

A cartridge mounting part 106 is provided on a front end part of the housing 10, and a cartridge 2 accommodating dental viscous materials A and B, which will be described later in conjunction with FIG. 6, is loaded onto the cartridge mounting part 106. In addition, two penetration holes 107, respectively penetrated by the two piston shafts 40, are formed in the front end part of the housing 10, as illustrated in FIG. 1 and FIG. 4.

The guide shaft 20 is made of a metal material, such as stainless steel or the like, for example, and is formed to a rod shape and is accommodated within the accommodating space 101 of the housing 10. One end of the guide shaft 20 is inserted into the front support hole 103 of the housing 10, and the other end of the guide shaft 20 is inserted into the rear support hole 105 of the housing 10. The guide shaft 20 is supported by the housing 10 so that an axial direction of the guide shaft 20 is parallel to the X1 and X2 directions. Further, the guide shaft 20 is supported by the housing 20 so that the guide shaft 20 is movable in the front and rear directions.

As illustrated in FIG. 2 and FIG. 3, a guide groove 201 is formed in the front end part of the guide shaft 20. An engaging piece 65 provided on the first slide bar 61, which will be described later, engages the guide groove 201. A first guide spring 25 which urges the guide shaft 20 in the X2 direction is provided in the front support hole 103 of the housing 10. In addition, a second guide spring 26 which urges the guide shaft 20 in the X2 direction between the rear end support wall 104 and an E-ring 202, is mounted on the rear end part of the guide shaft 20.

The slide block 30 is made of a metal material, such as an aluminum alloy or the like, for example, and is formed to a rectangular tube shape and is slidably mounted on the guide shaft 20. A front wall 301 of the slide block 30 is formed to project outward from the accommodating space 101 of the housing 10 through the opening 102, as illustrated in FIG. 2. A front wall hole 302 penetrated by the guide shaft 20, and a projecting part 303 projecting in the X2 direction from a back surface are formed in the front wall 301. In addition, a rear wall hole 306 penetrated by the guide shaft 20 is formed in a rear wall 305 of the slide block 30.

A release plate 308 is provided between the front wall 301 and the rear wall 305 of the slide block 30. The release plate 308 is made of a metal material, such as stainless steel or the like, for example, and is provided with a penetration hole 309 penetrated by the guide shaft 20. In addition, a slide spring 310 is provided between the release plate 308 and the rear wall 305, and the guide shaft 20 penetrates the slide spring 310.

A lower end of the release plate 308 is urged in the X1 direction by the slide spring 310 to approach the front wall 301, and an upper end of the release plate 308 contacts the projecting part 303 of the front wall 301. Hence, as illustrated in FIG. 2 and FIG. 3, the release plate 308 is in a tilted state in which the upper end is positioned to the rear of the lower end. When the release plate 308 tilts in this manner, an inner peripheral surface defining the penetration hole 309 and an outer peripheral surface of the guide shaft 20 make contact, and friction is generated between the release plate 308 and the guide shaft 20. Due to the friction generated between the release plate 308 and the guide shaft 20, the slide block 30 is in a state as if the slide block 30 were fixed to the guide shaft 20.

In addition, when the upper end of the release plate 308 is pushed frontward toward the front wall 301 by the user of the dispenser 1, the release plate 308 turns using the projecting part 303 of the front wall 301 as a fulcrum. As a result, the lower end of the release plate 308 pushes the slide spring 310 rearward, and the release plate 308 assumes a state parallel to the YZ-plane. When the release plate 308 is pushed and assumes a state standing perpendicularly to the axial direction of the guide shaft 20, the slide block 30 is released from a frictional force between the release plate 308 and the guide shaft 20, and assumes a state movable frontward and rearward.

The piston shafts 30 are made of a metal material, such as stainless steel or the like, for example, and is formed to a rod shape. The rear end part of each piston shaft 40 is fixed to the front wall 301 of the slide block 30, and the front end part of each piston shaft 40 penetrates the penetration hole 107 in the housing 10, as illustrated in FIG. 4. When the dispenser 1 is operated by the user, each piston shaft 40 projects in the X1 direction from the penetration hole 107. In a state in which the cartridge 2 is mounted on the housing 10 as illustrated in FIG. 6, each projecting piston shaft 40 presses and moves frontward a viscous material pushing member 201*d* which will be described later, to push out the viscous materials A and B within the cartridge 2.

In this embodiment, two piston shafts 40 are provided. However, only one piston shaft 40 may be provided, or three or more piston shafts 40 may be provided. Further, a length, a cross sectional shape, or the like of the piston shaft 40 may be appropriately set according to a shape or the like of the cartridge 2 that is used.

As illustrated in FIG. 5, two damper cavities 110 are formed in the housing 10, to communicate with the two respective penetration holes 107 penetrated by the two piston shafts 40. Each damper hole 110 is provided to extend downward from the respective penetration hole 107. A damper spring 112 is provided in each damper hole 110. Each damper spring 112 is a coil spring that is compressed between a bottom surface of the damper hole 110 and the piston shaft 40.

Because the damper spring 112 is pushed against the piston shaft 40, a movement of the piston shaft 40 is restricted in the front and rear directions by a frictional force between the damper spring 112 and the piston shaft 40. In addition, a movement of the slide block 30 to which the piston shaft 40 connects, is similarly restricted in the front and rear directions by the frictional force between the damper spring 112 and the piston shaft 40.

The handle 50 is made of a resin material such as an engineering plastic or the like, or a light and strong material such as a light metal that may be an aluminum alloy or the like, for example, and is formed to project downward from the housing 10. The handle 50 is formed to a rectangular tube shape with an open front end, so that the bar cover 60 can be accommodated in the handle 50.

A shape of the handle 50 is not limited to that of the example in this embodiment, and the handle 50 may have any shape that is easy to hold by the user of the dispenser 1. In this embodiment, the housing 10 and the handle 50 are formed integrally. However, the housing 10 and the handle 50 may be formed as separate parts.

The first slide bar 61 and the second slide bar 62 are made of a metal material, such as stainless steel, for example, and are formed to a rod shape. As illustrated in FIG. 2 and FIG. 3, one end of the first slide bar 61 is rotatably supported by the housing 10, and the other end of the first slide bar 61 is rotatably supported on the lever 70. The engaging piece 65 that engages the guide groove 201 of the guide shaft 20 is formed in the end part of the slide bar 61 closer to the housing 10. One end of the second slide bar 62 is rotatably supported on the handle 50, and the other end of the second slide bar 62 is rotatably supported on the lever 70.

The bar cover 60 is made of a resin material such as engineering plastic or the like, or a light and strong material such as a light metal that may be an aluminum alloy or the like, for example, and is formed to a rectangular tube shape, to accommodate the first slide bar 61 and the second slide bar 62.

The lever 70 is made of a resin material such as an engineering plastic or the like, or a light and strong material such as a light metal that may be an aluminum alloy or the like, for example. The lever 70 is connected to the housing 10 and the handle 50, by the first slide bar 61 and the second slide bar 62. The first slide bar 61 and the second slide bar 62 are rotated when the lever 70 is operated by the user of the dispenser 1 to move closer to the handle 50 or to move farther away from the handle 50. A shape of the lever 70 is not limited to that of the example in this embodiment, and the lever 70 may have any shape that is easy for the user of the dispenser 1 to squeeze the lever 70 together with the handle 50.

FIG. 6 is a view in a partial cross section illustrating an example of a state in which the cartridge 2 is mounted on the dispenser 1 in one embodiment. As illustrated in FIG. 6, the cartridge 2 includes two tubular bodies 201*a*. Each tubular body 201*a* has an opening 201*c* at a rear end thereof, and has an internal cross sectional shape that is constant and is inserted with the viscous material pushing member 201*d*. The two tubular bodies 201*a* accommodate the viscous materials A and B, respectively, that are different types of viscous materials that generate a chemical reaction when mixed. Rear ends of the openings 201*c* are closed by the respective viscous material pushing members 201*d*. A mixing tool 205 that mixes the viscous materials A and B is mounted at the front of the cartridge 20. For example, a viscous material accommodating cartridge proposed in Patent Document 2 may be used as the cartridge 2.

Next, a description will be given of the dispenser 1 in this embodiment.

When the user of the dispenser 1 squeezes the lever 70 from the state (FIG. 2) in which the lever 70 is separated from the handle 50 toward the direction approaching the handle 50, that is, a pulling operation is made to move the lever 70 rearward (FIG. 3), the first slide bar 61 rotates counterclockwise around a center part that is rotatably supported on the housing 10. When the first slide bar 61 rotates in this manner, the engaging piece 65, formed to project upward from the upper end of the first slide bar 61 and engaging the guide groove 201 of the guide shaft 20, also rotates. When the engaging piece 65 rotates counterclockwise, the guide shaft 20 moves frontward by being pushed by the engaging piece 65 that engages the guide groove 201.

In a case in which the guide shaft 20 moves frontward, a frictional force that is greater than the frictional force between the piston shaft 40 and the damper spring 112 is generated between the outer peripheral surface of the guide shaft 20 and the inner peripheral surface of the release plate 308 that is in the tilted state due to the lower end of the release plate 308 being pressed frontward by the slide spring 310 as described above. For this reason, the slide block 30 moves frontward together with the piston shaft 40 in the state as if the slide block 30 were fixed to the guide shaft 20 as described above.

As illustrated in FIG. 6, when the piston shaft 40 moves frontward together with the slide block 30 as described above in the state in which the cartridge 2 is mounted on the cartridge mounting part 106 at the front end part of the housing 10, the viscous material pushing members 201*d* of the cartridge 2 move frontward by being pushed by the piston shafts 40. As a result, the viscous materials A and B filled in the cartridge 2 are mixed by the mixing tool 205, and the viscous materials A and B in the mixed state are pushed frontward from the mixing tool 205 through a nozzle 206.

When the user of the dispenser 1 operates the lever 70 so as to release the lever 70 from the state illustrated in FIG. 3, the guide shaft 20 is pushed back by the first guide spring 25 and the second guide spring 26 and moves rearward, to return to the position illustrated in FIG. 2 before the lever 70 was pulled. When the guide shaft 20 moves rearward in this manner, the engaging piece 65 engaging the guide groove 201 is pushed rearward. In addition, the first slide bar 61 rotates clockwise around the center part that is rotatably supported on the housing 10, and the lever 70 returns to the initial position separated from the handle 50.

When the guide shaft 20 starts to move rearward in this manner, the lower end of the release plate 308 of the slide block 30 that is in the state as if the slide block 30 were fixed to the guide shaft 20 due to the friction as described above, is pushed rearward by the guide shaft 20. As a result, the release plate 308 approaches the state standing perpendicularly to the axial direction of the guide shaft 20, and the frictional force between the inner peripheral surface of the release plate 308 and the outer peripheral surface of the guide shaft 20 decreases. For this reason, the frictional force generated between the piston shaft 40 and the damper spring 112 becomes greater than the frictional force between the release plate 308 and the guide shaft 20, and the state as if the slide block 30 were fixed to the guide shaft 20 due to the friction is eliminated. Accordingly, the slide block 30 and the piston shaft 40 thereafter remain at the respective positions, and only the guide shaft 20 moves rearward.

As described above, when the user pulls the lever 70 rearward, the guide shaft 20, the slide block 30, and the piston shaft 40 move frontward. In addition, when the lever 70 moves frontward and returns, the slide block 30 and the piston shaft 40 remain in the respective positions, and only the guide shaft 40 moves rearward to return to the original position. Hence, when the user operates the lever 70, the slide block 30 and the piston shaft 40 move frontward, and predetermined amounts of the materials A and B are pushed out from the cartridge 2. When the user operates the lever 70 repeatedly, that is, alternately repeats the operations of pulling the lever 70 rearward and returning the lever 70 frontward (that is, releases the lever 70), it is possible to successively push out the materials A and B from the cartridge 2, the predetermined amounts at a time.

The amounts of the materials A and B pushed out from the cartridge 2 are determined by moving distances of the piston shafts 40 according to the operation of the lever 70. The moving distances of the piston shafts 40 according to the operation of the lever 70 may be appropriately set by a rotation angle of the first slide bar 61, shapes of the engaging piece 65 and the guide groove 201, or the like.

When replacing the cartridge 2, the user of the dispenser 1 holds the upper end part of the front wall 301 of the slide block 30 and the upper end part of the release plate 308, so as to pinch the two upper end parts by the user's fingertips. In this state, the upper end part of the release plate 308 is pushed toward the front wall 301, and the release plate 308 assumes the state perpendicular to the guide shaft 20. In this state, the slide block 30 is released from the frictional force between the penetration hole 309 of the release plate 308 and the guide shaft 20, and the slide block 30 assumes the state movable frontward and rearward with respect to the guide shaft 20.

The user of the dispenser 1 pulls the slide block 30 rearward and downward, while pinching the upper end part of the front wall 301 of the slide block 30 and the upper end part of the release plate 308 by the user's fingertips, to pull out and remove the piston shafts 40 from the cartridge 2.

After the piston shafts 40 are pulled out and removed from the cartridge 2, the user cartridge 2 is removed from the housing 10. Then, a new cartridge 2 is mounted on the cartridge mounting part 106 of the housing 10, so that the dispenser 1 is again put into a usable state. After the new cartridge 2 is mounted, the user operates the lever 70 again. Hence, every time the piston shafts 40 move frontward, the materials A and B filled in the cartridge 2 are pushed out, the predetermined amounts at a time.

For example, when a shell diameter of the cartridge 2 mounted on the dispenser 1 or a hole diameter of the nozzle 206 is small, an internal pressure of the cartridge 2 may gradually rise as the piston shafts 40 move frontward. When the internal pressure of the cartridge 2 rises in this manner, the materials may leak from the cartridge 2 due to the internal pressure after the user stops operating the dispenser 1.

In the dispenser 1 of this embodiment, the movements of the piston shafts 40 in the front and rear directions are restricted as described above by the friction between the piston shaft 40 and the damper spring 112. For this reason, when the internal pressure of the cartridge 2 becomes high and a force in the X2 direction greater than the frictional force between the piston shaft 40 and the damper spring 112 is applied to the piston shaft 40, the piston shafts 40 are pushed by the materials A and B within the cartridge 2 and move rearward, to decrease the internal pressure of the cartridge 2. Hence, according to the dispenser 1 in this embodiment, it is possible to effectively reduce the materials leaking from the cartridge 2 when the dispenser 1 is not operated, because the piston shafts 40 move rearward according to the internal pressure of the cartridge 2.

In addition, in the dispenser 1 of this embodiment, the handle 50 is formed to project from the housing 10, and the user can hold the handle 50 and operate the lever 70. For this reason, the user of the dispenser 1 can finely adjust the direction, the position, or the like of the materials A and B that are ejected from the cartridge 2, with ease. In addition, according to the dispenser 1 in this embodiment, the operability is improved, because the operation of the slide block 30, the replacement of the cartridge 2, or the like can be made in the state in which the user holds the handle 50.

The dispenser, and the dispenser and cartridge are described above by referring to the embodiments. However, the present invention is not limited to these embodiments, and various variations and modification may be made without departing from the scope of the present invention.

DESCRIPTION OF THE REFERENCE NUMERALS

1 Dispenser
2 Cartridge
10 Housing
20 Guide shaft
25 First guide spring
26 Second guide spring
30 Slide block
40 Piston shaft
50 Handle
60 Bar cover
61 First slide bar
62 Second slide bar
65 Engaging piece
70 Lever
112 Damper spring
301 Front wall
305 Rear wall
308 Release plate
310 Slide spring This International Application is based upon and claims priority to Japanese Patent Application No. 2016-109927, filed on Jun. 1, 2016, the entire contents of which are incorporated herein by reference.

The invention claimed is:

1. A dispenser comprising:

a guide shaft;

a housing, accommodating the guide shaft, and supporting the guide shaft movably in mutually opposite first and second directions along an axial direction of the guide shaft;

a slide block slidably mounted on the guide shaft;

a piston shaft having a first end mounted on the slide block, and a second end, opposite to the first end, projecting from the housing as the slide block moves in the first direction;

a handle projecting from the housing in a direction non-parallel to the axial direction of the guide shaft;

a slide bar having a third end rotatably supported on the housing, and a fourth end, opposite to the third end, approaching the handle when the slide bar is rotated in a rotating direction around the third end;

a lever, rotatably supported on the fourth end of the slide bar, and squeezable with respect to the handle; and an engaging piece provided on the third end of the slide bar and engaging a guide groove formed in the guide shaft, wherein the engaging piece moves the guide shaft in the first direction when the slide bar is rotated in the rotating direction around the third end to approach the handle.

2. The dispenser according to claim 1, wherein:

the slide block includes a release member having one end provided with an engaging part that engages the guide shaft, and a slide spring pressing the one end of the release member in the first direction, the one end of the release member is pressed by the slide spring to tilt the release member when the guide shaft moves in the first direction, to thereby engage the engaging part of the release member to the guide shaft, and generate a frictional force between the release member and the guide shaft, so that the slide block and the piston shaft mounted on the slide block move in the first direction due to the frictional force as the guide shaft moves in the first direction, and the one end of the release member moves in the second direction when the guide shaft starts to move in the second direction, against a pressing force of the slide spring due to the frictional force between the release member and the guide shaft as the guide shaft moves in the second direction, and the release member approaches a state perpendicular to the guide shaft, to decrease the frictional force between the release member and the guide shaft at the engaging part, so that the slide block and the piston shaft mounted on the slide block thereafter no longer move in the second direction as the guide shaft moves in the second direction.

3. A dispenser and cartridge, comprising:

a dispenser according to claim 2; and a cartridge including a pushing member that moves according to a movement of the guide shaft of the dispenser in the first direction, to push out a material filled inside the cartridge, wherein the material filled inside the cartridge is successively pushed out by alternately repeating a first operation in which a user rotates the slide bar in the rotating direction so that the fourth end of the slide bar approaches the handle and the piston shaft moves in the first direction due to the frictional force as the guide shaft moves in the first direction due to the engaging piece, and a second operation in which the user releases the slide bar so that the fourth end of the slide bar moves away from the handle and the piston shaft no longer moves in the second direction as the guide shaft moves in the second direction, after the guide shaft starts to move in the second direction due to the engaging piece and the release member approaches the state perpendicular to the guide shaft to decrease the frictional force.

4. The dispenser and cartridge as claimed in claim 3, wherein:

the slide bar rotates in the rotating direction to approach the handle when the user squeezes the lever with respect to the handle during the first operation, and the slide bar rotates in a direction to move away from the handle when the user releases the lever with respect to the handle during the second operation.

5. A dispenser and cartridge, comprising:

a dispenser according to claim 1; and a cartridge including a pushing member that moves according to a movement of the guide shaft of the dispenser in the first direction, to push out a material filled inside the cartridge.

6. The dispenser as claimed in claim 1, wherein the slide bar rotates in the rotating direction to approach the handle when a user squeezes the lever with respect to the handle.

7. The dispenser as claimed in claim 6, wherein the slide bar rotates in a direction to move away from the handle when the user releases the lever with respect to the handle.

8. A dispenser comprising:

a guide shaft;

a housing, accommodating the guide shaft, and supporting the guide shaft movably in mutually opposite first and second directions along an axial direction of the guide shaft;

a slide block slidably mounted on the guide shaft;

a piston shaft having a first end mounted on the slide block, and a second end, opposite to the first end, projecting from the housing as the slide block moves in the first direction;

a handle projecting from the housing in a direction non-parallel to the axial direction of the guide shaft;

a slide bar having a third end rotatably supported on the housing, and a fourth end, opposite to the third end, approaching the handle when the slide bar is rotated in a rotating direction around the third end;

a lever, rotatably supported on the fourth end of the slide bar, and squeezable with respect to the handle; and an engaging piece provided on the third end of the slide bar and engaging a guide groove formed in the guide shaft, wherein the engaging piece moves the guide shaft in the first direction when the slide bar is rotated in the rotating direction around the third end to approach the handle, wherein the housing has an elongated shape extending parallel to the axial direction of the guide shaft, and including a first part and a second part, the first part is located closer toward the first direction than a center of the elongated shape of the housing along the axial direction, the second part is located closer toward the second direction than the center of the elongated shape of the housing along the axial direction, the handle projects from the first part of the housing in the direction non-parallel to the axial direction of the guide shaft, and the third end of the slide bar is rotatably supported at the first part of the housing.

9. The dispenser as claimed in claim 8, wherein the slide bar rotates in the rotating direction to approach the handle when a user squeezes the lever with respect to the handle.

10. The dispenser as claimed in claim 9, wherein the slide bar rotates in a direction to move away from the handle when the user releases the lever with respect to the handle.

* * * * *